(12) United States Patent
Eng

(10) Patent No.: US 8,222,192 B2
(45) Date of Patent: Jul. 17, 2012

(54) ALCOHOL-BASED SKIN CLEANSER

(75) Inventor: William Eng, Tampa, FL (US)

(73) Assignee: R&W Medical LLC, Tampa, FL (US)

( * ) Notice: Subject to any disclaimer, the term of this patent is extended or adjusted under 35 U.S.C. 154(b) by 0 days.

(21) Appl. No.: 12/488,048

(22) Filed: Jun. 19, 2009

(65) Prior Publication Data

US 2010/0323939 A1 Dec. 23, 2010

(51) Int. Cl.
| | | |
|---|---|---|
| C11D 7/26 | (2006.01) | |
| C11D 7/44 | (2006.01) | |
| C11D 7/50 | (2006.01) | |
| C11D 3/20 | (2006.01) | |
| C11D 3/37 | (2006.01) | |
| C11D 3/382 | (2006.01) | |
| C11D 3/43 | (2006.01) | |

(52) U.S. Cl. ........ 510/130; 510/137; 510/138; 510/159; 510/420; 510/421; 510/437; 510/463

(58) Field of Classification Search .................. 510/130, 510/137, 138, 159, 108, 161, 420, 421, 437, 510/463
See application file for complete search history.

(56) References Cited

U.S. PATENT DOCUMENTS

| | | | |
|---|---|---|---|
| 3,131,153 A | | 4/1964 | Klausner |
| 3,864,472 A | * | 2/1975 | Pensak et al. .................... 424/54 |
| 3,876,759 A | * | 4/1975 | Pensak et al. .................... 424/58 |
| 3,947,570 A | * | 3/1976 | Pensak et al. .................... 424/54 |
| 4,645,662 A | * | 2/1987 | Nakashima et al. ............. 424/52 |
| 4,657,758 A | * | 4/1987 | Goldemberg et al. .......... 424/49 |
| 4,820,698 A | | 4/1989 | Degenhardt et al. |
| 4,847,072 A | | 7/1989 | Bissett et al. |
| 4,939,284 A | | 7/1990 | Degenhardt |
| 5,629,006 A | | 5/1997 | Hoang et al. |
| 5,874,068 A | * | 2/1999 | Engelman et al. ............... 424/54 |
| 6,821,507 B2 | * | 11/2004 | Glandorf et al. ................ 424/57 |
| 6,884,763 B2 | | 4/2005 | Willard et al. |
| 7,007,338 B2 | * | 3/2006 | Garabedian et al. ............ 15/231 |
| 7,199,090 B2 | | 4/2007 | Koivisto et al. |
| 7,842,726 B2 | * | 11/2010 | Aoki et al. .................... 514/547 |
| 2004/0096414 A1 | * | 5/2004 | Mori et al. .................. 424/70.16 |
| 2004/0132630 A1 | * | 7/2004 | Yamada et al. ................ 510/383 |
| 2004/0213821 A1 | * | 10/2004 | Suginaka et al. ............. 424/401 |
| 2006/0234886 A1 | * | 10/2006 | Massaro et al. ............... 510/130 |
| 2006/0263306 A1 | * | 11/2006 | Pan .................. 424/53 |
| 2007/0053849 A1 | * | 3/2007 | Doyle et al. .................... 424/50 |
| 2007/0196324 A1 | * | 8/2007 | Keefe et al. ................ 424/78.03 |
| 2008/0008665 A1 | * | 1/2008 | Ramji et al. ..................... 424/48 |
| 2008/0175800 A1 | * | 7/2008 | Schoening et al. ............. 424/49 |
| 2008/0253976 A1 | * | 10/2008 | Scott et al. ...................... 424/49 |
| 2009/0023620 A1 | * | 1/2009 | Ochomogo et al. .......... 510/106 |
| 2009/0087501 A1 | * | 4/2009 | Cummins ..................... 424/729 |
| 2010/0135927 A1 | * | 6/2010 | Hughes et al. .................. 424/50 |
| 2010/0135933 A1 | * | 6/2010 | Baig et al. ....................... 424/57 |

FOREIGN PATENT DOCUMENTS

KR 2005019942 A * 3/2005

OTHER PUBLICATIONS

Chemblink. 2010. "(S)-(+)-1,2-Propanediol." Accessed on Dec. 18, 2010 at http://www.chemblink.com/products/4254-15-3.htm.
Wikipedia. 2010. "Polyacrylamide." Accessed on Dec. 18, 2010 at http://en,wikipedia.org/wiki/Polyacrylamide.
Sigma-Aldrich Co. 2010. "Material Safety Data Sheet." Sigma-aldrich.com. Product name: Polycrylamide. Product No. 92560. pp. 1-5.
SCIENCELAB.COM, Inc. 2010. "Material Safety Data Sheet Methacrylic Acid MSDS." Sciencelab.com. Product name: Methacrylic Acid. Catalog code: SLM1918. pp. 1-6.
Abstract, Int J Cosmet Sci. Oct. 28, 2006(5):359-70. Accessed on Feb. 1, 2012 at http://www.ncbi.nlm.nih.gov/pubmed/18489300.
Arthur C. Guyton and John E. Hall "Textbook of Medical Physiology", 11th ed. Elsevier Saunders (2006) p. 794.

* cited by examiner

*Primary Examiner* — Lorna M Douyon
(74) *Attorney, Agent, or Firm* — Caroline Wei-Berk

(57) ABSTRACT

The invention provides a composition for cleansing skin comprising an emulsifiable organic solvent, such as ethanol or isopropyl alcohol, water, sodium benzoate, and a natural essential oil comprising a complex solution of compounds derived from a plant having topical antimicrobial activity. Natural essential oils useful as antimicrobials include tea tree, oregano, patchouli, rosemary, lemongrass, rose geranium, wild lavender, clove, lemon, *eucalyptus*, palmarosa, sandalwood, ravensara, and thyme. The cleanser may optionally include emollients, fragrances, thixotropic agents, chelating agents, antioxidants, and surfactants, such as glycerin, and propylene glycerol.

9 Claims, 7 Drawing Sheets

ALCOHOL-BASED SKIN CLEANSER

FIELD OF INVENTION

This invention relates to an antibiotic/antifungal composition. Specifically, the invention is an alcohol-based antibiotic/antifungal composition.

BACKGROUND OF THE INVENTION

Human health is negatively impacted by many microbial entities. Inoculation by fungi and bacteria can cause a wide variety of sicknesses and ailments. It is well known that the washing of hard surfaces, food (e.g. fruit or vegetables) and skin, especially the hands, with antimicrobial or non-medicated soap, can remove many fungi and bacteria from the these surfaces, thereby reducing the chances of fungi or bacterial inoculation. Removal of the fungi and bacteria is due to the surfactants within the soap and the mechanical action of the wash procedure. For this reason, it is recommended that people wash frequently to reduce the spread of fungi and bacteria.

Antibacterial cleansing products have been marketed in a variety of forms, including antibacterial soaps, hard surface cleaners, and surgical disinfectants. Rinse-off antimicrobial soaps have been formulated to provide bacteria removal during washing. Such conventional antibacterial cleansing products have been shown to also provide a residual effectiveness against some common gram-positive bacteria. Active antimicrobial agents are deposited during washing onto the cleansed surface and residual active ingredients control the viability and growth of some surviving and some newly contacted transient bacteria. For example, antibacterial soap, when used regularly in hand washing, has been found to provide a 90% to 97% reduction in gram-positive bacteria after two to five hours. Unfortunately, some topical antibacterial agents such as pyrithiones, thiazolones, sulfites, diazo compounds, chlorinated organics, brominated organics, phenols, bisphenols, resourcinols, and alkylated parabens have been linked to antibiotic resistant bacteria.

Many cleansing formulations that are currently available in the marketplace are nonabrasive "waterless" skin cleansers, meaning water does not have to be added during the hand cleansing process. The waterless cleansers currently commercially available typically use both polar and nonpolar ingredients, and have a gelatinous or paste-like, high viscosity consistency. The gelatinous consistency of the cleanser has been essential in such waterless hand cleansers to achieve the continuous cleansing action, due to extended contact between the cleanser and the skin. If the cleanser were liquid instead of gel, the cleanser would not adequately bind to the skin and provide continuous cleansing. The lower viscosity of a liquid cleanser can also cause the cleanser to run off of the hands, thereby facilitating the potential waste of cleanser. Therefore, waterless skin cleaners use a gelatinous or highly viscous consistency. These hand cleanser formulations also typically contain one or more antibacterial compounds to provide resistance to bacterial buildup and a degree of hand "sanitization" when they are used. Antimicrobial liquid cleansers are disclosed in U.S. Pat. No. 4,847,072, Bissett et al, issued Jul. 11, 1989; U.S. Pat. No. 4,939,284, Degenhardt, issued Jul. 3, 1990; and U.S. Pat. No. 4,820,698, Degenhardt, issued Apr. 11, 1989).

Ethanol and/or Isopropyl alcohol-based compositions require at least 60% percent volume/volume (v/v) (approximately 52% by weight to volume (wt/v)) to be useful for antibacterial or disinfecting purposes. Further, due to the disinfecting characteristics of alcohol, it is perceived that the higher the content the better the product.

Industrial and hand cleansing formulations typically contain a surfactant that solubilizes or emulsifies the oils, debris, and soil present on a substrate. These formulations inherently have oil-cleansing limitations when oil-emulsifiability or solvency alone is used as a cleaning mechanism. The alcohol-based disinfectant solutions are thickened, typically with use paraffin, lanolin or waxes, to eliminate the waste and facilitate spreading. However, use of thickened gels leaves a tacky feeling on the skin that builds up after repetitive use, making it necessary to wash off the thickeners before continuing the usage of an alcohol antiseptic solution.

Cleansers with high alcohol content are useful to disinfect, but require alcohol levels of at least 60%. According to Klausner, in U.S. Pat. No. 3,131,153, if more than 64% alcohol is used then a non-homogeneous compositions is obtained. A non-irritant skin disinfecting high alcohol content formulation for use as a skin-washing agent was attained by combining emulsifiers, surfactants and skin emollients to be used as a gel or ointment as described in U.S. Pat. No. 5,629,006.

SUMMARY OF THE INVENTION

A cleanser composition is described comprising an emulsifiable organic solvent, 1 to 10 total weight percent sodium benzoate, 0.01 to 1 total percent (v/v) natural essential oil, and 5 to 70 total percent (v/v) water. The emulsifiable organic solvent is ethanol, isopropyl alcohol, phenoxy ethanol, octanol, acetylated lanolin alcohol, 2-propanol, or n-propanol in some embodiments. The natural essential oil may be at least one oil derived from of tea tree, oregano, patchouli, rosemary, lemongrass, rose geranium, wild lavender, clove, lemon, *eucalyptus*, palmarosa, sandalwood, ravensara, and thyme. In specific embodiments, the natural essential oil is oregano at 0.02 percent (v/v).

The cleanser composition also optionally includes glycerol, glycerin, or propylene glycerol. In certain embodiments glycerin is included between 0.2 and 10 percent (v/v), and more specific embodiments included at 5 percent (v/v). Embodiments using propylene glycerol options use the propylene glycerol between 1 and 5 percent (v/v). The cleanser may also include at least one additional component, such as an emollient, fragrance, thixotropic agent, chelating agent, antioxidant, or at least one surfactant. In specific embodiments, surfactants used optionally include is methyl amines, ethyl amines, butyl amines, hexyl amines, TEA-stearate, TEA-oleate, TEA soyate, oleic acid, stearic acid, palmitic acid, myristic acid, coconut acid, and ethoxylated aliphatic alcohols.

Also disclosed in a cleanser formulation comprising an emulsifiable organic alcohol, 2 to 10 total weight percent sodium benzoate, 0.01 to 1 total percent (v/v) of oregano oil, and 5 to 70 total percent (v/v) water. The emulsifiable organic alcohol is, in specific embodiments, ethanol, isopropyl alcohol, phenoxy ethanol, octanol, acetylated lanolin alcohol, 2-propanol, or n-propanol The cleanser composition of claim 13, further comprising at least one compound selected from the group consisting of glycerol, glycerin, and propylene glycerol. In specific embodiments, glycerin is added at 5 percent (v/v). In embodiments using propylene glycerol, propylene glycerol is added between 1 and 5 percent (v/v). The cleanser may also include at least one additional component selected from the group consisting of: emollient, fragrance, thixotropic agent, chelating agent, antioxidant, and at least one surfactant.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
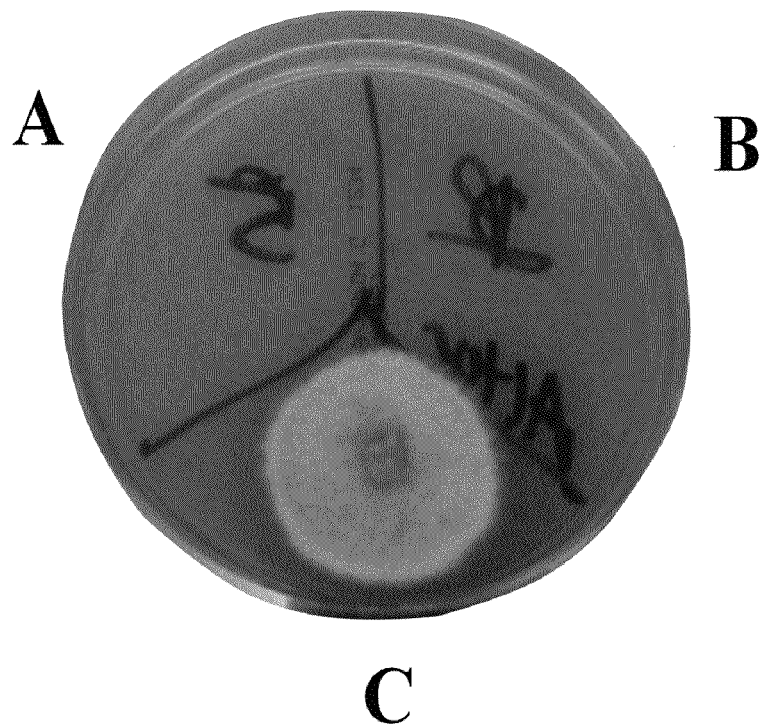
FIG. 1 is an image of a blood agar plate inoculated with *Trichophyton rubrum* and overlaid with (A) 0.05% oregano in the present invention (B) 0.02% oregano in the present invention or (C) no treatment (positive control).

Disclosed is a skin cleanser that effectively disinfects skin of microbes and fungi. The present skin cleanser is derived from sodium benzoate, oregano and ethyl, alcohol, glycerin and surprisingly allows compositions with lower alcohol content to provide protection from microbes and fungi. The composition described is in the form of a liquid or gel, however foamable compositions are envisioned within the scope of the invention, such as when the composition is mixed with additional constituents as described in U.S. Pat. No. 7,199,090. The composition delivers a liquid or gel of the appropriate consistency to be readily spread on skin without dripping. This composition is around 60% v/v alcohol provides an effective disinfectant. Specific embodiments of the invention include glycol, glycerin, or lanolin from 1 to 20 total weight percent to improve consistency and provide lubrication and protection from humidity.

A formulation according to the present invention also optionally includes a wide range of additional ingredients compounds including abrasives, antioxidants, chelating agents, colorants, astringents, fragrances, preservatives, pH adjusting agents and sunscreen. The CTFA International Cosmetic Ingredient Dictionary, 6th Edition, 1995 details a wide variety of nonlimiting cosmetic ingredients commonly found in skincare products that are suitable for use herein.

As used herein, the term "antimicrobial activity" is defined to include an inhibition zone of at least two millimeters around a colony of pathogenic or potentially pathogenic skin colonizing gram-positive, gram-negative or fungal organisms on an agar plate where a test substance is applied to a planar colony at a concentration of 0.5 micro-liters per square centimeter of organism growth medium surface area, following 24 hours of incubation.

As used herein, the term "Target Hand Sanitizer", "Target hand sanitizer", or "THS" is defined as an alcohol-based sanitizer composition (Target, Minneapolis, Minn.) consisting of 62% ethyl alcohol active ingredient. Inactive ingredients are listed as benzophenone-4, carbomer, fragrance, glycerin, isopropyl myristate, propylene glycol, tocopheryl acetate, and water The active natural essential oil component of the antimicrobial composition is formulated into a variety of waterless hand cleaner formulations that include oregano, surfactants and detergents; fragrances; perfumes; water; and thickeners such as glycerin or propylene glycol. The skin cleaner formulation contains an emulsifiable organic alcohol solvent that is compatible with human skin contact. The organic alcohol solvent is present from 50 to 65 total weight percent. Exemplary organic solvents include, ethanol, phenoxy ethanol, octanol, acetylated lanolin alcohol, 2-propanol, or n-propanol. The invention anticipates that a single alcohol may be used or that a blend of two or more alcohols may comprise the alcohol content of the composition either for a gel-like or foamable product.

A surfactant may also be present in the waterless hand cleanser formulation to form an emulsion between the emulsifiable organic solvent and water present in the formulation. The surfactant may be any water-soluble or water dispersible nonionic, anionic, cationic, or an amphoteric compound with emulsifying abilities. Representative surfactants and properties may be found in Remington's Pharmaceutical Sciences, 17th edition (Mack Publishing Company). The choice of surfactant is selected based on cleansing requirements and the ability to afford a stable gelatinous state in the presence of a given concentration of oregano. Exemplary surfactants include methyl, ethyl, butyl and hexyl amines, triethanol amine (TEA)-stearate, TEA-oleate and TEA soyate. Other exemplary surfactants are fatty acid surfactants, such as oleic, stearic, palmitic, myristic, coconut acid, and ethoxylated aliphatic alcohols, where the base alcohol contains from 6-24 carbon atoms in straight or branched chain configuration. A lower ratio of ethoxylation to base compound typically results in a stiffer gel composition with better high temperature stability. In contrast, a higher ethoxylation to base compound ratio of generally greater than 7:1 tends to afford water solubility.

Optionally, a stabilizer is provided in order to improve shelf and stress stability and modify gel viscosity. A stabilizer according to the present invention includes any conventional stabilizer and includes thickeners, hydrogenated vegetable oils, or an inorganic particulate dispersant. Non-limiting examples include guar gums; anionic, nonionic, cationic and lipophilic modified guar gums having a molecular weight of 1,000-1,000,000; polyacrylic acids, methacrylic acids, cellulose resins, polyethylene glycols, hydroxy alkyl celluloses, carboxy alkyl celluloses, polyalkylene amines, such as polyethylene amine, starches, modified starches; salts thereof; and combinations thereof each having molecular weights ranging from about 1,000 to 4,000,000.

Water is typically present from 5 to 50 total weight percent. In preparing the formulation, oil phase containing organic solvents and other lipophilic components are mixed with a water phase. Dissolution of the surfactant and the oregano oil in either the oil phase or water phase is known to one skilled in the art based upon the specific identities thereof.

EXAMPLES

The Examples were prepared to illustrate the ability to produce alcohol-based formulations which can be dispensed using different volumes of oregano in a solution of water, 62% ethanol, and sodium benzoate. All parts and percentages are expressed by volume unless otherwise indicated.

To compare the effectiveness of oregano, blood agar plates (see below for details) were divided into regions and streaked with *Serratia odorifera* (Vitec quality control collection, catalog number 33077); *Klebsiella pneumoniae* (Vitec quality control collection, catalog number 13883); *Enterococcus faecalis* (Vitec quality control collection, catalog number 51299); *Staphylococcus aureus* (Vitec quality control collection, catalog number 29213); *Escherichia coli* (Vitec quality control collection, catalog number 25922); *Pseudomona aeruginosa* (Vitec quality control collection, catalog number 10231); *Proteus vulgaris* (Vitec quality control collection, catalog number 49132); *Proteus mirabilis* (Vitec quality control collection, catalog number 9002); *Acinetobacter baumannii* (Vitec quality control collection, catalog number 19606); *Candida albicans* (Vitec quality control collection, catalog number 10231); *Alternaria* spp, *Trichophyton rubrum*, *Shigella* spp, and *Salmonella* spp were patient isolates. Methicillin-resistant *Staphylococcus aureus* (MRSA) was obtained from five clinical isolates obtained from 3 males and 2 females. The patient's age ranged from 17 to 86 years old, with two isolates were from the buttock, another two from the arm, and one was from the leg.

Bacteria were suspended in sterile saline to a standard 1 McFarland for gram positive organisms, 0.5 McFarland for gram negatives, and 3 McFarland for yeast. The microorganism suspension was plated onto BBL-TSA with 5% SB plates (Benton Dickinson, Sparks, Md.). Two 6 mm blank paper disks (Becton Dickinson, Sparks, Md.) were sterilely placed on each plate, and then impregnated directly with 5 μL of oregano extract (*Origanum vulgare*, Ananda Apothecary (Boulder, Colo.) or overlaid with a drop of cleanser. In studies using MRSA, a BBL Sensi-Disc (oxacillin 1 μg) served as a confirmation control. These plates were incubated overnight at 30° C. for 16-24 hours. The diameter of the zone of inhibition surrounding the disk was measured (mm). A sterile loop was used to scrap the zone of inhibition that was then inoculated to a fresh blood plate. These plates were incubated overnight at 30° C. and examined the next day for growth to determine if the inhibition of growth was due to bacteriostatic or bactericidal action. Microbial growth was measured by visual inspection, seen in Table 1.

Figure 2:
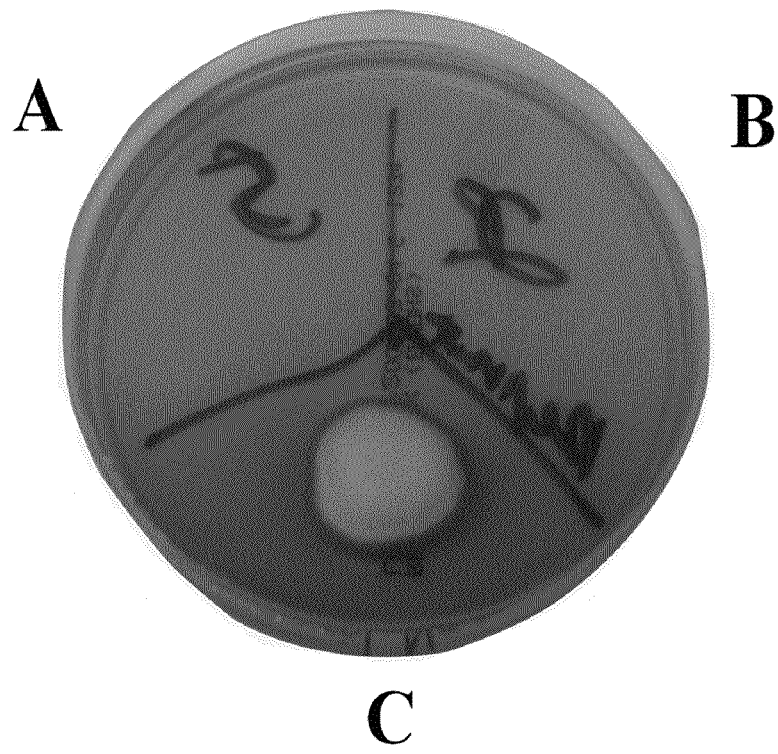
FIG. 2 is an image of a blood agar plate inoculated with a dermatophyte and overlaid with (A) 0.05% oregano in the present invention (B) 0.02% oregano in the present invention or (C) no treatment (positive control).
Figure 3:
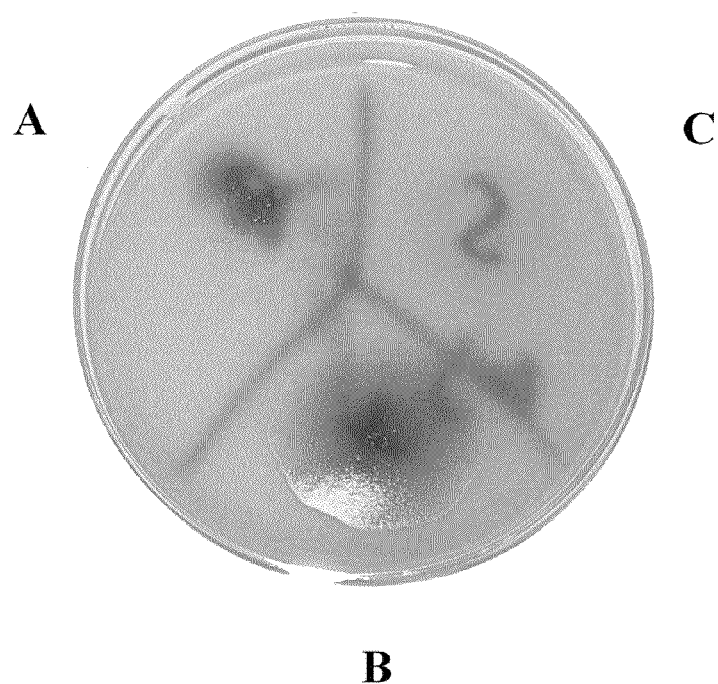
FIG. 3 is an image of a blood agar plate inoculated with *Shigella* spp and overlaid with (A) 62% ethyl alcohol-based sanitizer (B) no treatment (positive control) or (C) the present invention.
Figure 4:
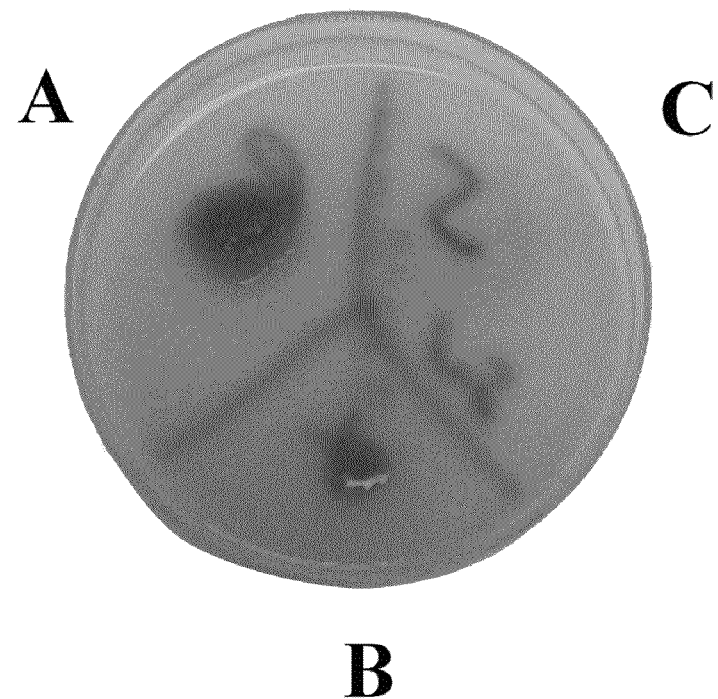
FIG. 4 is an image of a blood agar plate inoculated with *Salmonella* spp and overlaid with (A) 62% ethyl alcohol-based sanitizer (B) no treatment (positive control) or (C) the present invention.
Figure 5:
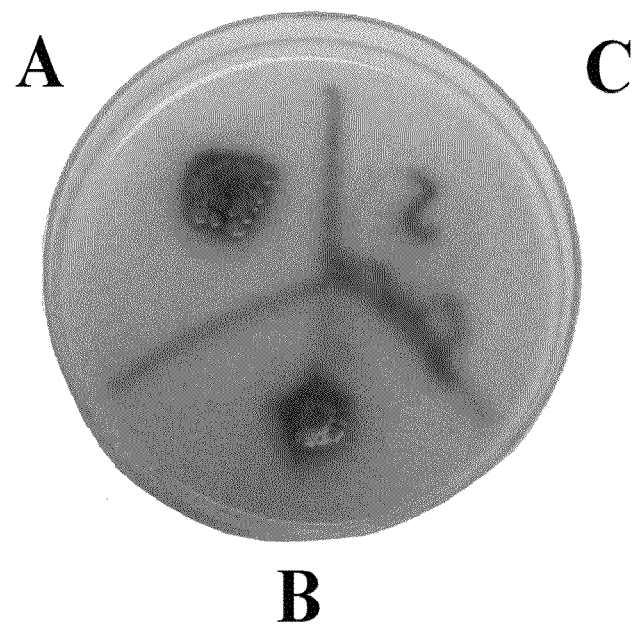
FIG. 5 is an image of a blood agar plate inoculated with *Serratia oderifera* and overlaid with (A) 62% ethyl alcohol-based sanitizer (B) no treatment (positive control) or (C) the present invention.
Figure 6:
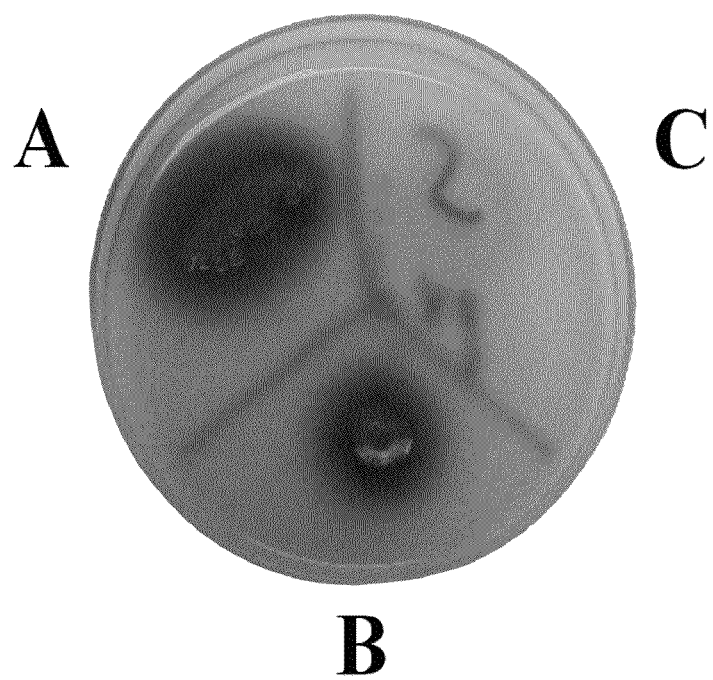
FIG. 6 is an image of a blood agar plate inoculated with *Proteus vulgaris* and overlaid with (A) 62% ethyl alcohol-based sanitizer (B) no treatment (positive control) or (C) the present invention.
Figure 7:
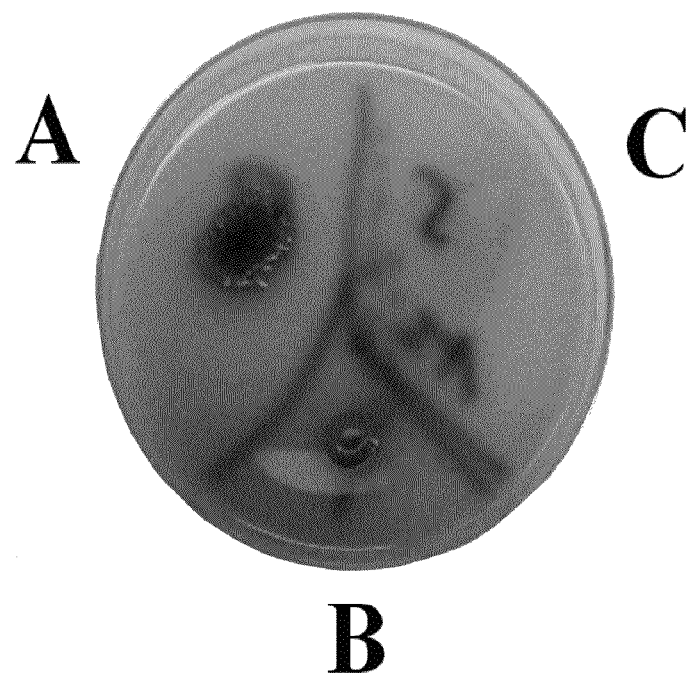
FIG. 7 is an image of a blood agar plate inoculated with *Ascinetobacter baummanni* and overlaid with (A) 62% ethyl alcohol-based sanitizer (B) no treatment (positive control) or (C) the present invention.
Figure 8:
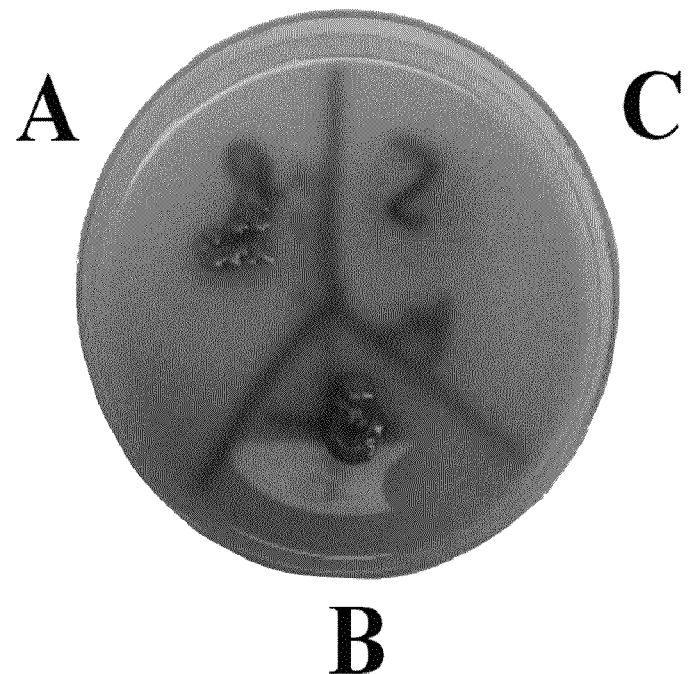
FIG. 8 is an image of a blood agar plate inoculated with *Klebsiella pneumoniae* and overlaid with (A) 62% ethyl alcohol-based sanitizer (B) no treatment (positive control) or (C) the present invention.
Figure 9:
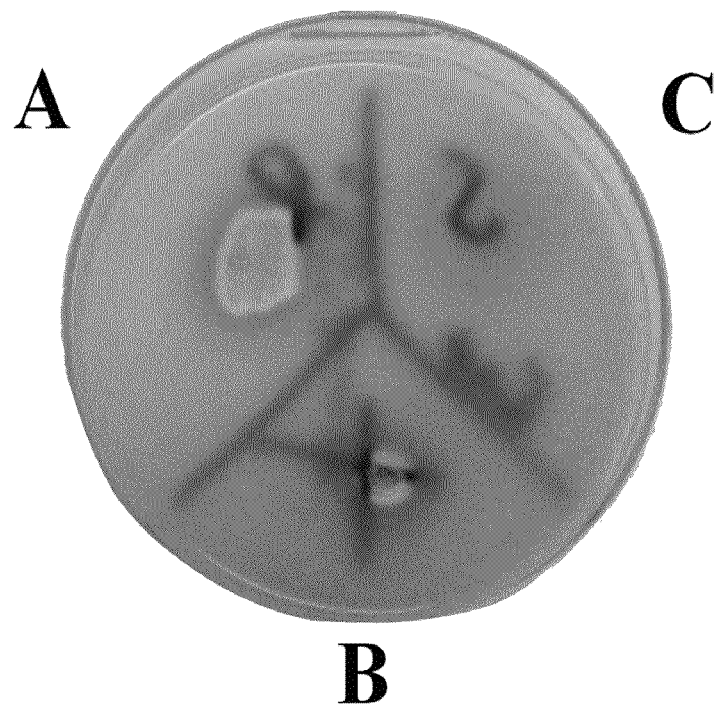
FIG. 9 is an image of a blood agar plate inoculated with *Enterococcus faecalis* and overlaid with (A) 62% ethyl alcohol-based sanitizer (B) no treatment (positive control) or (C) the present invention.
Figure 10:
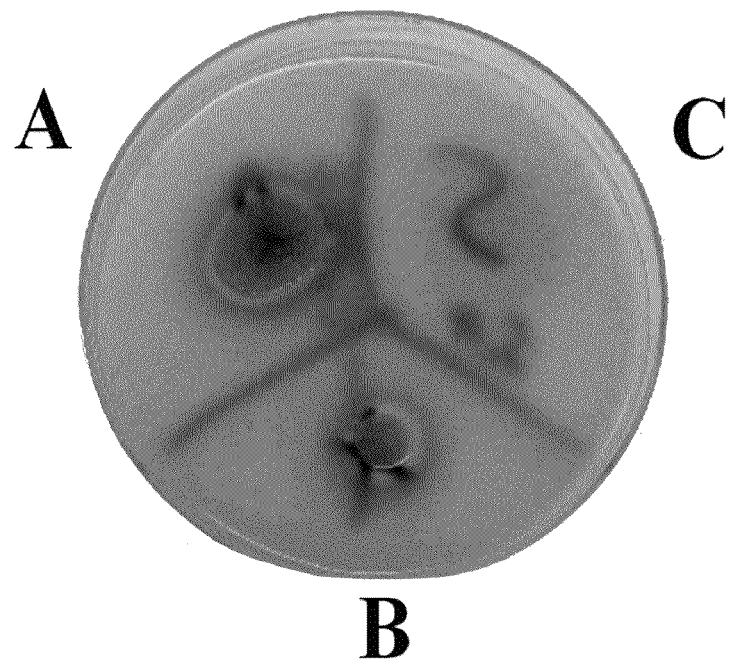
FIG. 10 is an image of a blood agar plate inoculated with *Staphlococcus aureus* and overlaid with (A) 62% ethyl alcohol-based sanitizer (B) no treatment (positive control) or (C) the present invention.
Figure 11:
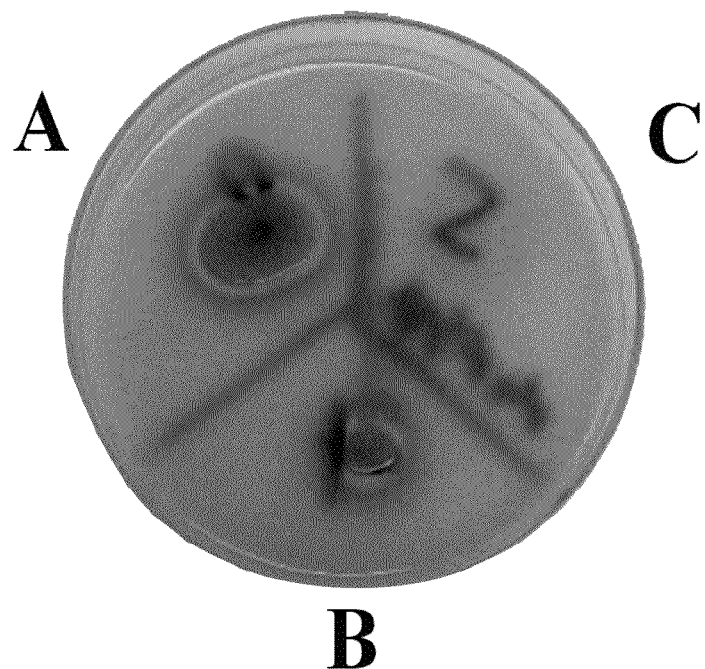
FIG. 11 is an image of a blood agar plate inoculated with Methicillin resistant *Staphylococcus aureus* (MRSA) and overlaid with (A) 62% ethyl alcohol-based sanitizer (B) no treatment (positive control) or (C) the present invention.
Figure 12:
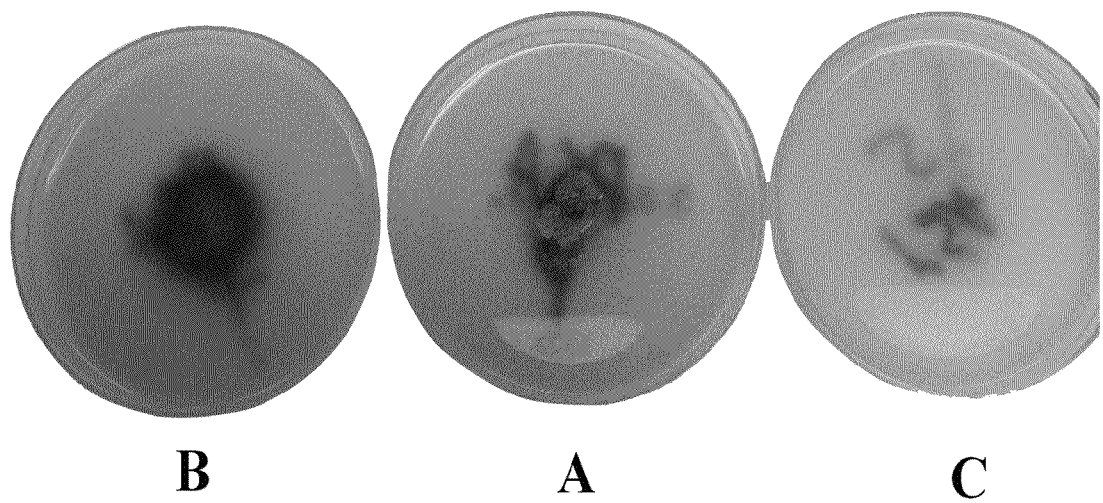
FIG. 12 is an image of blood agar plates inoculated with *Pseudomonas aeruginosa* and overlaid with (A) 62% ethyl alcohol-based sanitizer (B) no treatment (positive control) or (C) the present invention.
Figure 13:
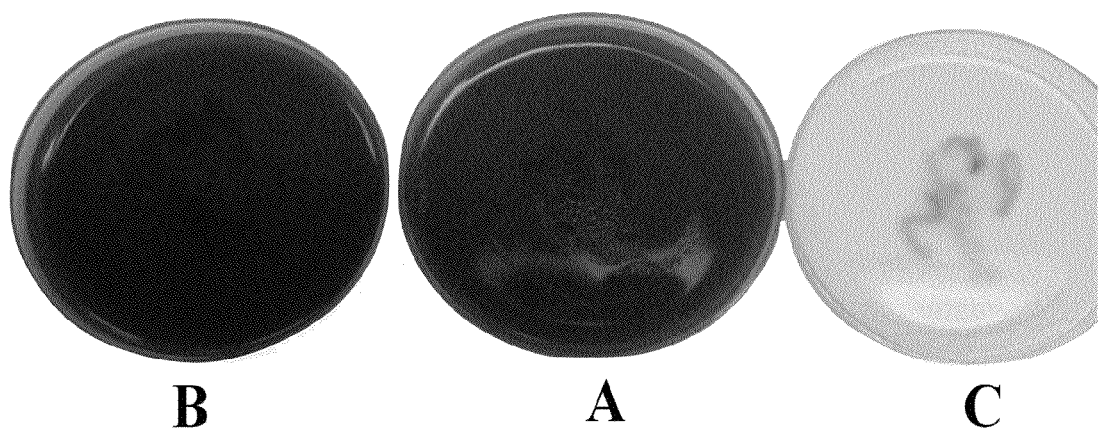
FIG. 13 is an image of blood agar plates inoculated with *Proteus mirabilis* and overlaid with (A) 62% ethyl alcohol-based sanitizer (B) no treatment (positive control) or (C) the present invention.

The addition of 5 μL of oregano extract showed an average diameter of the zone of inhibition (mm) in descending order for each microorganism was: *K. pneumonia*, 36; *E. faecalis*, 30; *A. baumannii*, 27.5; MRSA, 25.5; *S. aureus*, 22; *P. vulgaris*, 22; *P. mirabilis*, 20; *E. coli*, 19; *C. albicans*, 18; *S. odorifera*, 14.5; and *P. aeruginosa*, 0. For *S. aureus* and MRSA, oregano was bacteriostatic, but it was bactericidal to all other microorganisms except for *P. aeruginosa* which showed no inhibition, see FIGS. 1 and 2.

Blood agar plates were made using agar medium of 15 g enzymatic digested casein, 4 g enzymatic digested animal tissue, 2 g yeast extract, 1 g corn starch, 5 g sodium chloride, and 14 g agar, suspended in 1 L purified water. The medium was heated and defibrinated sheep blood added to the agar medium to 5% of the total volume. The blood agar was aliquoted to plates and allowed to cool.

One embodiment of the natural antibiotic was the development of an oregano ointment that was custom compounded with a petroleum base by Westchase Pharmacy (Tampa, Fla.). All preparations were performed in an ISO 7 room by licensed pharmacists as with all other preparations described in this application. The oregano extract (Ananda Apothecary, Boulder, Colo.) was tested for quality control analysis using gas chromatography, indicating the extract is composed of alpha-thujene 0.43%, alpha-pinene 0.26%, 1-octen-3-ol 0.12%, myrcene 0.71%, alpha-terpinene 0.68%, para-cymene 2.58%, limonene 0.15%, gamma-terpinene 3.02%, thymol 0.61%, carvacrol 83.05%, and beta-caryophyllene 0.72%. The white petrolatum USP base was obtained (E. Fougera, Melville N.Y.), consisting of a mixture of saturated hydrocarbons (alkanes). Oregano ointments were prepared at 0.1, 0.5, 1, 2, 3, 4, 5, 10, 20, 40, 60, and 80% concentrations. For comparison, a generic triple antibiotic ointment consisting of neomysin sulfate 5 mg/1 g, polymyxin B sulfate 5000 u, and bacitracin zinc 400 u in a white petroleum base (E. Fougera & Co, Melville N.Y.) and NEOSPORIN®, ORIGINAL (Pfizer, Morris Plains N.J.) was also tested against all microorganisms. A positive control consisting solely of petroleum ointment was also tested. Three antiseptic solutions were also examined; Isopropyl alcohol 91%, Hydrogen peroxide 3%, and Povidone iodine 10% (all from Walgreen, Deerfield Ill.). The studies were repeated twice to ensure reproducibility.

Microorganisms were placed on top of the blood agar plate, and they were overlaid with a test compound. After 24 hours incubation at 30 C, the plates were examined for growth. No inhibition was seen for any microorganism at oregano ointment concentrations of 0.1 or 0.5%. At 1% oregano, *K. pneumoniae* and *E. coli* were inhibited. At 5% oregano, *E. faecalis*, *C. albicans*, and *A. baumannii* were inhibited. Ointments with 10% oregano showed inhibition of *S. aureus* and *S. odorifera*. Ointments with 20% oregano inhibited *P. vulgaris* and *mirabilis*. It is noted that *P. aeruginosa* was not inhibited at any concentration tested.

Further, four of the five MRSA strains were inhibited at ointments with oregano levels of 10%, 20%, 40%, 60% and 80%, but not at 5% oregano. One strain of MRSA was inhibited at 20% and higher concentrations, but not at 5 and 10% oregano.

Generic triple antibiotic ointment and Neosporin® were found to reduce the growth rate of all organisms tested. However, all tested organisms were eventually able to overcome the antibiotics. An ointment that consisted of only petroleum base and hydrogen peroxide showed no inhibitory properties. Isopropyl alcohol completely inhibited the growth of *K. pneumoniae* and retarded the growth of the other 10 organisms. Povidone iodine showed complete inhibition of *K. pneumonia, C. albicans, P. vulgaris*, and *S. odorifera*, but retarded the growth of the other 7 organisms.

The results of the disk diffusion studies did not show perfect correlation with the minimal inhibitory concentration from the ointment studies. This may be due to variations in the interactions between the microorganism and the solubility of oregano in its ointment base. In ointment form, the studies showed that a higher concentration (10%) is required than those reported in broth studies (<2%) to inhibit *S. aureus* (Nostro A, et al. Effects of oregano, carvacrol and thymol on *Staphylococcus aureus* and *Staphylococcus epidermidis* biofilms. *J Med Microbiol*, 2007; 5:519-523; Preuss H G, et al. Minimum inhibitory concentrations of herbal essential oils and monolaurin for gram-positive and gram-negative bacteria. *Mol Cell Biochem*, 2005; 272:29-34; Nostro A, et al. Susceptibility of methicillin-resistant staphylococci to oregano essential oil, carvacrol and thymol. *FEMS Microbiol Lett*. 2004; 230:191-195; Hammer K A, et al. Antimicrobial activity of essential oils and other plant extracts. *J Appl Microbiol*. 1999; 86:985-990). However, for *E. coli*, the reported inhibitory concentrations (<2%) were comparable to these findings (1%). In one paper, the authors showed that the solubility of carvacol could be increased by dissolving it in ethanol, agar, or carrageenan, and this resulted in increased effectiveness in broth (Burt S A, et al. Increase in activity of essential oil components carvacrol and thymol against *Escherichia coli* O157:H7 by addition of food stabilizers. *J Food Prot*. 2005; 68:919-926).

Various essential oils (Ananda Apothecary, Boulder, Colo.) were next tested to determine their relative antimicrobial activity. Oils were obtained by steam distillation of the plant material. As before, blood agar plates were streaked with microbes; *S. aureus*, MRSA, *E. coli*, *Streptococcus pyrogens*, and *K. pneumonia*. A 5 uL drop of the oil composition was then placed onto the paper discs and incubated as before. The oils were evaluated for microbial inhibition potential from the zone of inhibition and whether the mechanism of was due to bacteriostatic or bactericidal action, as seen in Table 1.

TABLE 1

Comparison of antimicrobial activity of various essential oils against various bacteria.

| | Bacteria | | | | |
|---|---|---|---|---|---|
| Treatment Oil | *S. aureus* | *E. coli* | *S. pyrogens* | *K. pneumoniae* | MRSA* |
| Patchouli | S, 12 | NI | S, 4 | NI | S, 12 |
| Rosemary | S, 17.5 | C, 8 | NI | | NI |
| Tea tree | S, 13.5 | C, 16 | S, 9 | C, 30 | S, 10 |
| Lemongrass | S, 18 | C, 19 | S, 17.5 | NI | S, 20 |
| Rose geranium | S, 9 | NI | NI | | NI |
| Wild lavender | S, 11 | C, 9 | NI | | NI |
| Clove | S, 12 | C, 12 | S, 10 | | S, 13 |
| Lemon | S, 8 | NI | NI | | NI |
| Eucalyptus | S, 10 | S, 9 | | | NI |
| Palmarosa | S, 12 | NI | | | S, 11 |
| Sandalwood | S, 9 | NI | | | NI |
| Ravensara | S, 9 | S, 9 | | | NI |
| Oregano | S, 22 | S, 19 | C, 30 | C, 36 | S, 22.5 |
| Thyme | S, 20 | C, 19 | S, 15 | C, 21 | S, 21.5 |

NI = No inhibition
S = bacteriostatic
C = bactericidal
numbers indicate the average diameter of the zone of inhibition in millimeters Other plant extracts including tea tree and palmarosa also show no inhibition against *P. aeruginosa*, suggesting this organism possesses an innate property that permits it to thrive in extremely hostile conditions. It is also noted that the tests show oregano is bacteriostatic toward *S. aureus*. Other reports has shown oregano is generally bactericidal to microorganisms (Faleiro L, et al. Antibacterial and antioxidant activities of essential oils isolated from *Thymbra capitata* L. (Cav.) and *Origanum vulgare* L. *J Agric Food Chem*. 2005; 21:8162-8168 Friedman M, et al. Antibacterial activities of plant essential oils and their components against *Escherichia coli* O157:H7 and *Salmonella enterica* in apple juice. *J Agric Food Chem*. 2004; 52:6042-6048), which correlates with most findings of this study.

Observations of oregano on the blood agar plate showed that extensive lysis of the red blood cells occurs which would be consistent with the proposition that oregano acts as to disrupt cell membranes. The non-specific antimicrobial action of oregano would also reduce the possibility of developing drug resistance. While in vitro studies have been numerous, in vivo studies have been limited. One report showed that oregano could eradicate vaginal candidiasis in rats after 7 days of treatment (Chami F, et al. Evaluation of carvacrol and eugenol as prophylaxis and treatment of vaginal candidiasis in an immunosuppressed rat model. *J Antimicrob Chemother*. 2004; 54:909-914). However, tissue toxicity was not addressed. While many plants possess anti-microbial properties, not all may be suitable as antibiotics use due to adverse effects. An observation from these experiments is that the most potent extracts (oregano, thyme, lemongrass, tea tree, and palmarosa) caused lysis of the RBCs, which left a clearing in the agar plate. Thus, the preparations of essential oils would need to be dilated to minimize tissue toxicity.

Of the plant extract based ointment studies, a range of 5 to 20% oregano appears to be the most optimal anti-microbial concentration. Testing of various concentrations of oregano ointment showed that concentrations of oregano ointment at 20% or greater result in a mild burning sensation on an open wound comparable to the application of alcohol. In comparison to triple antibiotic preparations (generic and NEOSPORIN®), oregano ointment not only showed complete inhibition, but also broader activity.

Testing confirmed that an oregano-based ointment possesses some inhibitory effects against a wide range of microorganisms associated with skin infections. One notable exception is *P. aeruginosa*, however, others have reported that oregano could inhibit *P. aeruginosa* (Leeja L, Thoppil J E. Antimicrobial activity of methanol extract of *Origanum majorana* L. (Sweet marjoram). *J Environ Biol*. 2007; 1:145-146; Lambert R J, et al. A study of the minimum inhibitory concentration and mode of action of oregano essential oil, thymol and carvacrol. *J Appl Microbiol*. 2001; 91:453-462; Elgayyar M, et al. Antimicrobial activity of essential oils from plants against selected pathogenic and saprophytic microorganisms. *J Food Prot,* 2001; 64:1019-1024, Hammer K A, et al. Antimicrobial activity of essential oils and other plant extracts. *J Appl Microbiol.* 1999; 86:985-990).

Sodium benzoate was tested as an additive to the composition of an oregano gel. Starting with a base composition of 0.01% oregano in Target Hand Sanitizer, sodium benzoate was measured out and added at weight percentages of 1, 2, 5, and 10% concentrations. A cotton tip applicator soaked with microorganism suspension was swabbed over an area on the BBL-TSA with 5% SB plates. An antimicrobial-gel-free area on the plate was swabbed with microorganism to ensure that the test organisms were viable. Then various gel preparations were overlaid on top of the organisms. These plates were incubated at 30° C. and re-examined daily for 7 days for growth, seen in Table 2.

TABLE 2

Growth potential of bacteria and fungi with varying amounts of sodium benzoate in an oregano/THS composition.

| Bacteria/ Fungus | Amount of sodium benzoate (%) | | | | Positive control |
|---|---|---|---|---|---|
| | 1 | 2 | 5 | 10 | |
| S. aureus | − | − | − | − | +++ |
| MRSA* | +++ | − | − | − | +++ |
| E. faecalis | +++ | − | − | − | +++ |
| E. coli | +++ | − | − | − | +++ |
| K. pneumoniae | +++ | +++ | − | − | +++ |
| C. albicans | − | − | − | − | +++ |
| A. baumannii | +++ | − | − | − | +++ |
| P. vulgaris | + | − | − | − | +++ |
| S. odorifera | − | − | − | − | +++ |
| Salmonella spp | +++ | +++ | ++ | − | +++ |
| Shigella spp | +++ | − | − | − | +++ |
| P. aeruginosa | +++ | +++ | − | − | +++ |
| P. mirabilis | − | − | − | − | +++ |

*Methicillin resistant *Staphylococcus aureus*
− = no growth
+ = 1-2 colonies
++ = 3-5 colonies
+++ = over 5 colonies The results of indicated use of sodium benzoate at a minimum of 5% exhibits broad antibacterial and antifungal properties, inhibiting all but *Salmonella* spp. No growth was seen at 10% sodium benzoate, with oregano in a THS gel base. In gel form, the studies showed a small concentration (0.01%) of oregano is required to efficiently inhibit growth of microbes. It is noted that adding sodium benzoate significantly reduces the concentration of oregano required to inhibit microbial growth. By comparison, ointments of oregano began showing some inhibitory effect at 1% oregano (*K. pneumoniae* and *E. coli*) and required at least 5% oregano before significant inhibition was seen (*E. faecalis, C. albicans,* and *A. baumannii* were also inhibited).

Propylene glycol was also tested as an additive to the composition. A Krisgel comprising polyacrylamide, C13-C14 isoparaffin, laureth-7, xanthan gum, and hydroxypropylcellulose (PCCA, #30-3215) was used. A based was made with 0.1% oregano, 2% sodium benzoate and 62% ethanol. Propylene glycol was added to the base and streaked on BBL-TSA with 5% SB plates as before. Microorganisms were swabbed over an area that was later covered with the gel and an gel-free area on the plate was swabbed with microorganism to ensure that the test organisms were viable. These plates were incubated at 30° C. and re-examined daily for 7 days for growth. Microbial growth was determined by visual inspection, as seen in Table 3.

TABLE 3

Growth potential of bacteria and fungi with varying amounts of propylene glycol in an oregano/sodium benzoate/ethanol antibiotic/antifungal composition.

| Bacteria/ Fungus | Amount of propylene glycol (%) | | | | Positive control |
|---|---|---|---|---|---|
| | 0 | 1 | 2 | 5 | |
| S. aureus | + | + | + | + | +++ |
| MRSA* | + | + | + | + | +++ |
| E. faecalis | − | − | − | − | +++ |
| E. coli | + | + | + | + | +++ |
| K. pneumoniae | − | + | + | + | +++ |
| C. albicans | − | + | + | + | +++ |
| A. baumannii | − | + | + | + | +++ |
| P. vulgaris | − | + | + | + | +++ |
| S. odorifera | − | + | + | + | +++ |
| S. enteritidis | + | + | + | + | +++ |
| S. sonnei | − | + | − | + | +++ |
| P. aeruginosa | − | + | + | + | +++ |
| P. mirabilis | + | + | + | + | +++ |

*Methicillin resistant *Staphylococcus aureus*
− = no growth
+ = 1-2 colonies
++ = 3-5 colonies
+++ = over 5 colonies The addition of propylene glycol was found to reduce growth, but not completely inhibit it. This was curious, as propylene glycol has properties similar to those of ethylene glycol, which is used as a preservative and safer replacement to formaldehyde.

Example 2

The lower limits of oregano concentrations in an effective gel formulation were tested. Five grams of sodium benzoate was added to an Unguator® electronic mortar and pestle (Professional Compounding Centers of America, ON, Canada), with 5 ml glycerin, varying amounts of oregano, described below, and 89.98 ml of ethanol (to a final concentration of 62%), forming Composition A. The composition was calculated to contain 5% (wt/v) sodium benzoate, 5% glycerin, and 62% ethanol. Oregano was added at 0 ml, 0.01 ml, 0.02 ml, and 0.05 ml oregano. The skin cleanser composition was then mixed in the electronic mortar and pestle at 5,000 rpm for two minutes.

Bacteria and yeast (Viteck QC, Thermo Fisher Scientific Inc., Waltham, Mass., American Type Culture Collection, Manassas, Va.) were streaked over the blood agar plates and treatment zones defined on the plates. A drop of cleanser having between 0-0.05% oregano was overlaid on an appropriate treatment zone. The plates were then incubated at 30° C. for 16-24 hours, and microbial growth measured by visual inspection, seen in Table 4 and FIGS. 3-13.

TABLE 4

Growth potential of bacteria and fungi using varying amounts of oregano in the antibiotic/antifungal composition.

| Bacteria/Fungus | Amount of oregano (%) | | | | Positive control |
|---|---|---|---|---|---|
| | 0 | 0.01 | 0.02 | 0.05 | |
| S. aureus | +++ | + | − | − | +++ |
| MRSA* | +++ | − | − | − | +++ |
| E. faecalis | + | − | − | − | +++ |
| E. coli | + | − | − | − | +++ |
| K. pneumoniae | +++ | − | − | − | +++ |
| C. albicans | +++ | − | − | − | +++ |
| A. baumannii | +++ | − | − | − | +++ |
| P. vulgaris | − | − | − | − | +++ |
| S. odorifera | − | − | − | − | +++ |
| Salmonella spp | ++ | − | − | − | +++ |
| Shigells spp | +++ | − | − | − | +++ |
| P. aeruginosa | +++ | − | − | − | +++ |
| P. mirabilis | +++ | − | − | − | +++ |

*Methicillin resistant *Staphylococcus aureus*
− = no growth
+ = 1-2 colonies
++ = 3-5 colonies
+++ = over 5 colonies As seen in Table 4, 0.01% oregano inhibited growth of most microbes, but at least 0.02% oregano was needed to effectively limit growth of all microbes tested. Further, there was no noticeable difference between 0.02% oregano and higher concentrations. Comparison to compositions of just ethanol and oregano, which required concentrations of 10% oregano and 20% ethanol to exhibit any useful antimicrobial activity, Composition A provides efficient microbial inhibition with 0.02% oregano and about 60% ethanol. Further, unlike prior compositions of 10% oregano and 20% ethanol, the Composition A also inhibits *P. aerugnosa, K. pneumonia*, and *S. odorifera*.

Example 3

The skin cleanser composition was recreated, as described above, using 0.02% oregano. Five grams of sodium benzoate was added to the electronic mortar and pestle, with 5 ml glycerin, 0.02 ml oregano, and 89.98 ml of 62% ethanol. The skin cleanser composition was then mixed in the electronic mortar and pestle at 5,000 rpm for two minutes.

Bacteria and yeast (Viteck QC, Thermo Fisher Scientific Inc., Waltham, Mass., American Type Culture Collection, Manassas, Va.) were streaked over the blood agar plates and treatment zones defined on the plates. A drop of the 0.02% oregano cleanser or other skin cleanser was overlaid on an appropriate treatment zone, seen in Table 6. The plates were then incubated at 30° C. for 16-24 hours, and microbial growth measured by visual inspection, seen in Table 5.

TABLE 5

Growth potential of bacteria and fungi using the 0.02% oregano antibiotic/antifungal composition compared to Purell ® (Johnson & Johnson Consumer Companies, Inc., Langhorne, PA), Germ-X ® (Saint Louis MO), CleanWell ™ (CleanWell Co., San Francisco, CA), and Vicks ® (Proctor & Gamble, Co., Cincinnati, OH). A positive control (no antimicrobial agents) was also tested.

| Bacteria/Fungus | Antibacterial/Antifungal Treatment | | | | | |
|---|---|---|---|---|---|---|
| | 0.02% oregano | Purell ® | CleanWell ™ | GermX ® | Vicks ® | Positive control |
| S. aureus | − | + | + | + | − | + |
| MRSA* | − | + | + | + | − | + |
| E. faecalis | − | + | + | + | − | + |
| E. coli | − | + | + | + | − | + |
| K. pneumonia | − | + | + | + | − | + |
| C. albicans | − | + | + | + | + | + |
| A. baumannii | − | + | + | + | − | + |
| P. vulgaris | − | + | + | − | − | + |
| S. odorifera | − | + | + | + | + | + |
| Salmonella spp | − | + | + | + | − | + |
| Shigella spp | − | + | + | + | − | + |
| P. aeruginosa | − | − | − | − | + | + |
| P. mirabilis | − | + | + | − | − | + |

*Methicillin resistant *Staphylococcus aureus*
− = no growth
+ = colony growth/no inhibition of microbe The 0.02% oregano displays a broad spectrum anti-microbial activity. As seen in Table 5, the cleanser prevented growth of g-positive bacteria, g-negative bacteria, yeasts, and fungi. Further analysis of the 0.02% oregano-treated microbes indicated no viable organisms were recoverable after treatment, indicating the composition is bactericidal and fungicidal.

Example 4

Patients were asked to select one finger at random for testing. The selected finger was sprayed with the skin cleanser composition with 0.02% oregano. 5 wt % sodium benzoate, 5 wt % glycerin, 0.02% oregano, and 62% ethanol. A blood agar plate was divided into two regions, and the patient asked to place the finger coated in the skin cleanser to one region. The patient then selected a different finger and placed the finger onto the other region of the plate. The plate was then incubated at 30° C. for 16-24 hours, and microbial growth measured by visual inspection, seen in Table 6.

TABLE 6

Growth potential of bacteria and fungi from random region of patients hand using the 0.02% oregano antibiotic/antifungal composition (treatment) compared to no treatment. Results indicate the number of colonies on each agar plate.

| Patient | No treatment | With treatment |
|---|---|---|
| 1 | 9+ | 2+ |
| 2 | 30+ | 0 |
| 3 | 7+ | 0 |
| 4 | 3+ | 0 |
| 5 | 2+ | 0 |
| 6 | 0 | 2+ |
| 7 | 6+ | 1+ |
| 8 | 4++ | 5+ |
| 9 | 52+ | 2+ |
| 10 | 48+ | 20+ |
| 11 | 9+ | 28+ |
| 12 | 5+ | 1+ |
| 13 | 5+ | 10+ |
| 14 | 12+ | 14+ |
| 15 | 0 | 0 |
| 16 | 11+ | 12+ |
| 17 | 51+ | 5+ |
| 18 | 48+ | 1+ |
| 19 | 10+ | 1+ |

Bacterial and fungal growth were measured based on the number of colonies. For the non-treated fingers, the mean colony growth (16.4±18.8) was found to differ significantly from the amount of growth on treated fingers (5.47±7.89), using a paired student's t-test (t=2.44, p=0.025). The results confirm use of skin cleanser composition with 0.02% oregano, 5 wt % sodium benzoate, 5 wt % glycerin, 0.02% oregano, and 62% ethanol exhibits broad antibacterial and antifungal properties.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of an alcohol based antibiotic/antifungal composition, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A skin cleanser composition comprising
   a quantity of ethanol from about 60 to 65 weight percent;
   a quantity of water from 5 to 50 volume percent;
   a quantity of sodium benzoate from 5 to 10 weight percent;
   a quantity of glycerin from 5 to 10 volume percent;
   a stabilizer wherein the stabilizer is a carbomer of acrylic acid, or cellulose resin;
   and 0.01 to 1 volume percent of oregano oil.

2. The cleanser composition of claim 1, further comprising at least one compound selected from the group consisting of glycerin and propylene glycol.

3. The cleanser composition of claim 1, wherein the glycerin is 5 volume percent.

4. The cleanser composition of claim 2, wherein the propylene glycol is between 1 and 5 volume percent.

5. The cleanser composition of claim 1, further comprising the emulsifiable organic alcohol selected from the group consisting of phenoxy ethanol, octanol, acetylated lanolin alcohol, 2-propanol, and n-propanol.

6. The cleanser composition of claim 1, further comprising at least one additional component selected from the group consisting of: emollients, fragrance, pH adjusting agent, thixotropic agent, chelating agent, antioxidant, and at least one surfactant.

7. The cleanser composition of claim 6, wherein the surfactant is selected from the group consisting of methyl amines, ethyl amines, butyl amines, hexyl amines, TEA stearate, TEA oleate, TEA soyate, oleic acid, stearic acid, palmitic acid, myristic acid, coconut acid, and ethoxylated aliphatic alcohols.

8. The cleanser composition of claim 1, wherein the oregano oil is 0.02 to 1 volume percent.

9. The cleanser composition of claim 8, wherein the oregano oil is 0.02 volume percent.

* * * * *